(12) United States Patent
McGovern et al.

(10) Patent No.: US 8,491,587 B2
(45) Date of Patent: Jul. 23, 2013

(54) ADJUSTABLE OFFSET BUSHING

(75) Inventors: Michael A. McGovern, Wyckoff, NJ (US); Sujit Sivadas, Mahwah, NJ (US); Scott Logan, Ringwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1561 days.

(21) Appl. No.: 11/643,084

(22) Filed: Dec. 21, 2006

(65) Prior Publication Data

US 2008/0177337 A1 Jul. 24, 2008

(51) Int. Cl.
*A61F 2/30* (2006.01)

(52) U.S. Cl.
USPC ........................................... 606/86 R

(58) Field of Classification Search
USPC ................. 606/86 R, 102, 87–89, 95, 96–99
See application file for complete search history.

(56) References Cited

U.S. PATENT DOCUMENTS

| | | | | |
|---|---|---|---|---|
| 5,454,816 | A * | 10/1995 | Ashby | 606/88 |
| 5,484,446 | A * | 1/1996 | Burke et al. | 606/87 |
| 5,613,970 | A * | 3/1997 | Houston et al. | 606/88 |
| 5,676,668 | A * | 10/1997 | McCue et al. | 606/87 |
| 5,733,290 | A * | 3/1998 | McCue et al. | 606/86 R |
| 5,782,920 | A * | 7/1998 | Colleran | 623/20.34 |
| 5,941,884 | A * | 8/1999 | Corvelli et al. | 606/88 |
| 5,976,147 | A * | 11/1999 | LaSalle et al. | 606/88 |
| 6,033,410 | A * | 3/2000 | McLean et al. | 606/88 |
| 6,063,091 | A | 5/2000 | Lombardo et al. | |
| 6,159,216 | A * | 12/2000 | Burkinshaw et al. | 606/88 |
| 6,228,091 | B1 * | 5/2001 | Lombardo et al. | 606/88 |
| 6,355,045 | B1 * | 3/2002 | Gundlapalli et al. | 606/88 |
| 6,620,168 | B1 * | 9/2003 | Lombardo et al. | 606/88 |
| 6,916,325 | B2 * | 7/2005 | Kana et al. | 606/89 |
| 7,001,394 | B2 * | 2/2006 | Gundlapalli et al. | 606/88 |
| 7,022,141 | B2 * | 4/2006 | Dwyer et al. | 623/22.12 |
| 2005/0075638 | A1 * | 4/2005 | Collazo | 606/80 |
| 2006/0200163 | A1 * | 9/2006 | Roger et al. | 606/89 |

* cited by examiner

*Primary Examiner* — Kevin T Truong
*Assistant Examiner* — Christopher Beccia
(74) *Attorney, Agent, or Firm* — Lerner, David, Littenberg, Krumholz & Mentlik, LLP

(57) ABSTRACT

An orthopaedic instrumentation having an intermediate piece that has an opening for receiving an intramedullary reference. The intermediate piece such as a tibial template or a cutting guide is located on the resected tibia or femur in a manner that it optimally covers the resected surface of the tibia or the femur. A bushing guide is provided for mounting on the intermediate piece. The bushing guide has a circular opening. An offset bushing is rotatably mounted in the opening in the bushing guide. A trigger flange is slidably mounted on the offset bushing. The trigger flange can slide back and forth relative to the offset bushing. An indicia is formed on the upper surface of trigger flange. The indicia when aligned with one of the indicia on the offset bushing body measures the offset of center of a bore in the trigger flange from center of the offset bushing. The offset bushing can rotate around its longitudinal axis in the opening in the bushing guide. Indicia on the offset bushing may be used to measure the orientation of the center of the hole in the trigger with respect to the center of bushing body.

22 Claims, 7 Drawing Sheets

ADJUSTABLE OFFSET BUSHING

BACKGROUND OF THE INVENTION

The present invention relates to orthopaedic instrumentation, and, more particularly, relates to adjustable offset bushing that allows easy determination of offset magnitude and orientation of an offset stem of a femoral component or a tibial baseplate.

DESCRIPTION OF THE RELATED ART

Conventional tibial and femoral prosthetic implants have a stem extension which is essentially centrally located relative to a base portion. However, the centrally located stem may interfere with the tibial or femoral cortex as the surgeon attempts to center the implant on the tibia or the femur. The intramedullary (IM) canal of the tibia or femur is often not centrally located relative to the peripheral edges of the tibia or the femur. A centrally located stem on a tibial or femoral implant may therefore not allow a proper positioning of the base portion of the implant. Thus, it is necessary to determine the offset for the stem on the tibial or femoral implant.

U.S. Pat. No. 6,063,091 (the '091 patent) discloses an intramedullary tibia revision tool that include a collection of different sized tibial templates, each template adapted to receive an angular offset positioning guide, a collection of offset bushings, each bushing having a different offset distance. Once again, the instrumentation of the '091 patent would require multiple pieces of bushing to accurately determine the magnitude of the offset. A surgeon would be required to pursue trial and error method, switching between the different pieces until correct magnitude of the offset is determined such that optimal coverage of the resected surface of the tibia is obtained.

Thus, there is a need for an orthopaedic instrument that would allow determination of the correct magnitude of the offset without having to go through trial and error using multiple pieces.

SUMMARY OF THE INVENTION

The orthopaedic instrument of the present invention overcomes the shortcomings of the prior art. The orthopaedic instrument of the present invention includes a tibial template having an opening. The tibial template is located on the resected tibia in a manner that it optimally covers the resected surface of the tibia. A bushing guide is provided for mounting on the tibial template. The bushing guide has a handle connected to a body. The body has a circular opening. When the bushing guide and tibial template are assembled together, opening in the bushing guide and opening in the tibial template are substantially aligned. An offset bushing is rotatably mounted in the bushing guide. A trigger flange is slidably mounted on the offset bushing. The trigger flange can slide back and forth relative to the offset bushing. An indicia is formed on the upper surface of trigger flange. The indicia when aligned with one of the indicia on the offset bushing body measures the offset of center of a bore in the trigger flange from center of the offset bushing. The offset bushing body has a groove around its periphery. Multiple detents are formed in the groove. The offset bushing body forms a sliding fit in the opening in the bushing guide. The offset bushing can rotate around its longitudinal axis in the opening in the bushing guide. When detents are present, offset bushing rotates in the opening in a stepwise manner, with each step being the distance between adjacent detents. An indicia may be associated with one or more detents. Alignment of the indicia with a fixed point such as a pin may be used to measure the orientation of the center of the hole in the trigger with respect to the center of bushing body.

In another embodiment of the joint prosthesis instrument, an intramedullary reference like an intramedullary reamer, intramedullary rod, stem trial or stem extender shaft is inserted in a bone, for example, a femur. An intermediary piece such as a cutting guide is attached to the bone. A rotatable bushing is rotatably inserted in the intermediary piece. A trigger flange is slidably mounted in the bushing. The trigger flange has a first hole that allows the intramedullary reference to slide in the hole. By rotating the bushing and sliding the trigger flange the first hole in the trigger flange can be located in a position corresponding to the position of the intramedullary reference, thereby measuring the angular orientation and linear distance of the intramedullary reference with respect to a fixed point on the intermediate piece.

In use, the intermediate piece such as the tibial template, bushing guide and offset bushing are assembled together. Next, the assembly is passed over an intramedullary reference onto the bone. The tibial template is positioned for best coverage of the resected bone surface. This is achieved by rotating the bushing body and translating trigger flange to find the setting for which optimum bone coverage is obtained. Tibial template is pinned in this position and setting for offset is recorded by noting indicia on the offset bushing that corresponds to indicia on the trigger. The orientation is recorded by noting indicia on the offset bushing that corresponds to a fixed point on the bushing guide.

DETAILED DESCRIPTION

Figure 1:
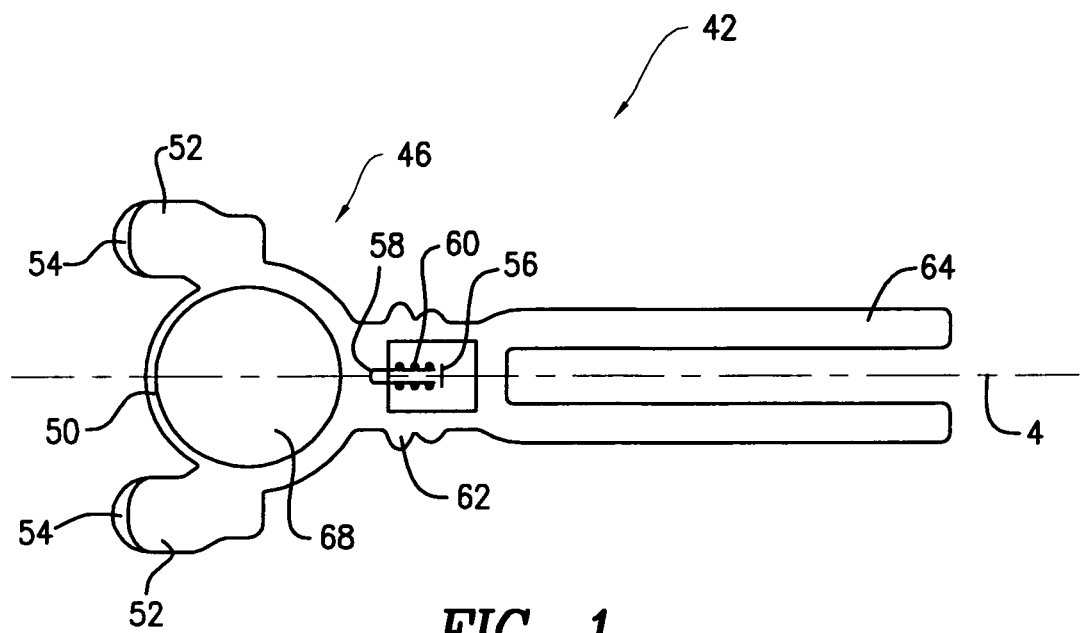
FIG. 1 is a plan view of a tibial template.

FIG. 1 shows a tibial template 30. Tibial template 30 has a body 32 and an opening 34 formed in body 32. Opening 34 includes branch sections 36 and ledges 38 formed in branch section 36. Tibial template 30 is to be located on resected proximal tibia in a manner that it optimally covers the resected surface of the tibia. A large substantially circular opening 40 is formed in tibial template 30. As used herein, when referring to bones or other parts of the body, the term "proximal" means closer to the heart and the term "distal" means more distant from the heart.

Figure 2:
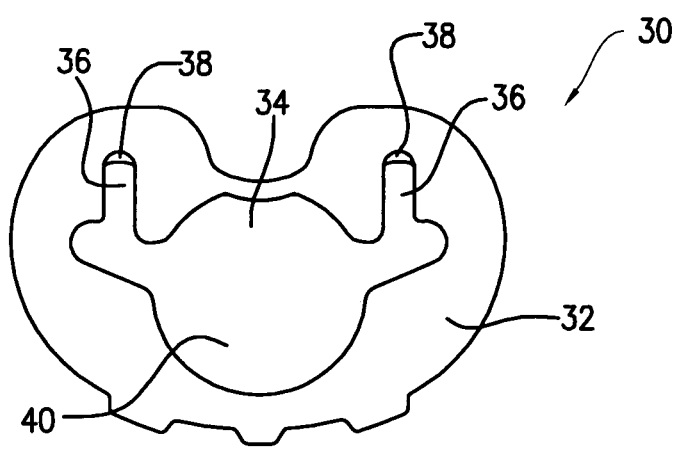
FIG. 2 is a plan view of a bushing guide that can mount on the tibial template of FIG. 1.

FIG. 2 shows a bushing guide 42. Bushing guide 42 has a handle 44 connected to a body 46. Body 46 has a circular opening 48 surrounded by a wall 50. Feet 52 project from wall

50. Feet 52 have a step 54 formed on each foot 52. Each step 54 engages under ledge 38 to attach bushing guide 42 to tibial template 30. When bushing guide 42 and tibial template 30 are assembled together, opening 40 and opening 48 are substantially aligned. However, it is not necessary that these openings align for the intended purpose of the instrumentation to be achieved.

A rectangular block 56 is formed on the portion of handle 64 that is close to body 46. A spring loaded pin 58 is mounted in the hollow inside rectangular block 56. Spring 60 forces pin 58 in a direction away from block 56, however, when a force is applied at the tip of pin 58, pin 58 can be moved towards the center of block 56.

A sliding block 62 is slidably attached to handle 44. Sliding lock 62 can slide along handle 44, and when it is in a location close to body 46 a projection (not shown) on sliding block 62 engages a projection on tibial template 30 to lock bushing guide 42 to tibial template 30.

Figure 2A:
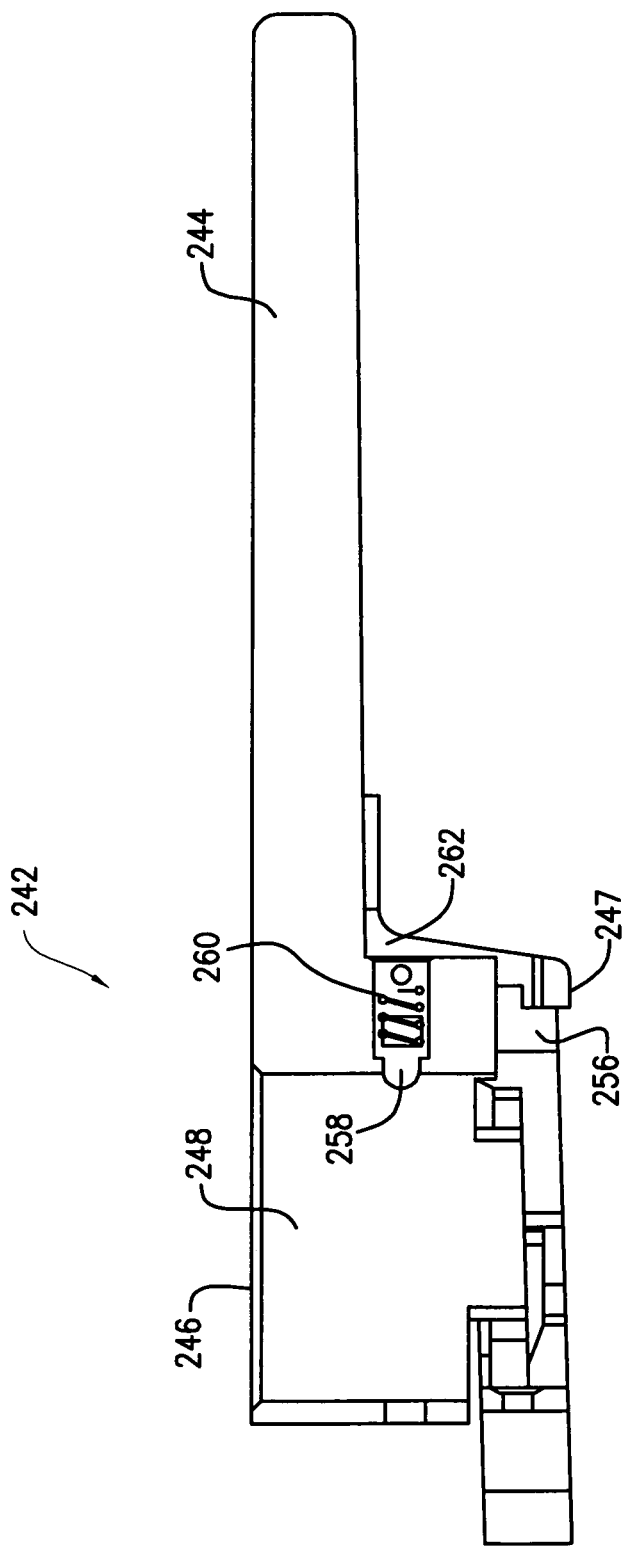
FIG. 2A is a side view of another embodiment of bushing guide that can mount on the tibial template of FIG. 1.

FIG. 2A is a side view of another embodiment of bushing guide 42. Bushing guide 242 of this embodiment has a handle 244 connected to a body 246. Bushing guide 242 is similar to bushing guide 242 except for the features discussed hereafter. A rectangular block 256 is made integral with handle 244 and is located close to body 246 on the bottom surface of handle 244. A spring loaded pin 258 is mounted in the hollow inside rectangular block 256. Spring 260 forces pin 258 in a direction away from block 256 and into an opening 248 formed in body 246. However, when a force is applied at the tip of pin 258, pin 258 can be moved towards the center of block 256. A sliding block 262 is slidably attached to handle 244. Sliding lock 262 can slide along handle 244, and when it is in a location close to body 246 a projection 247 on sliding block 262 engages a projection on tibial template 30 to lock bushing guide 242 to tibial template 30. The method of use of bushing guide 42 and 242 are generally similar.

Figure 3:
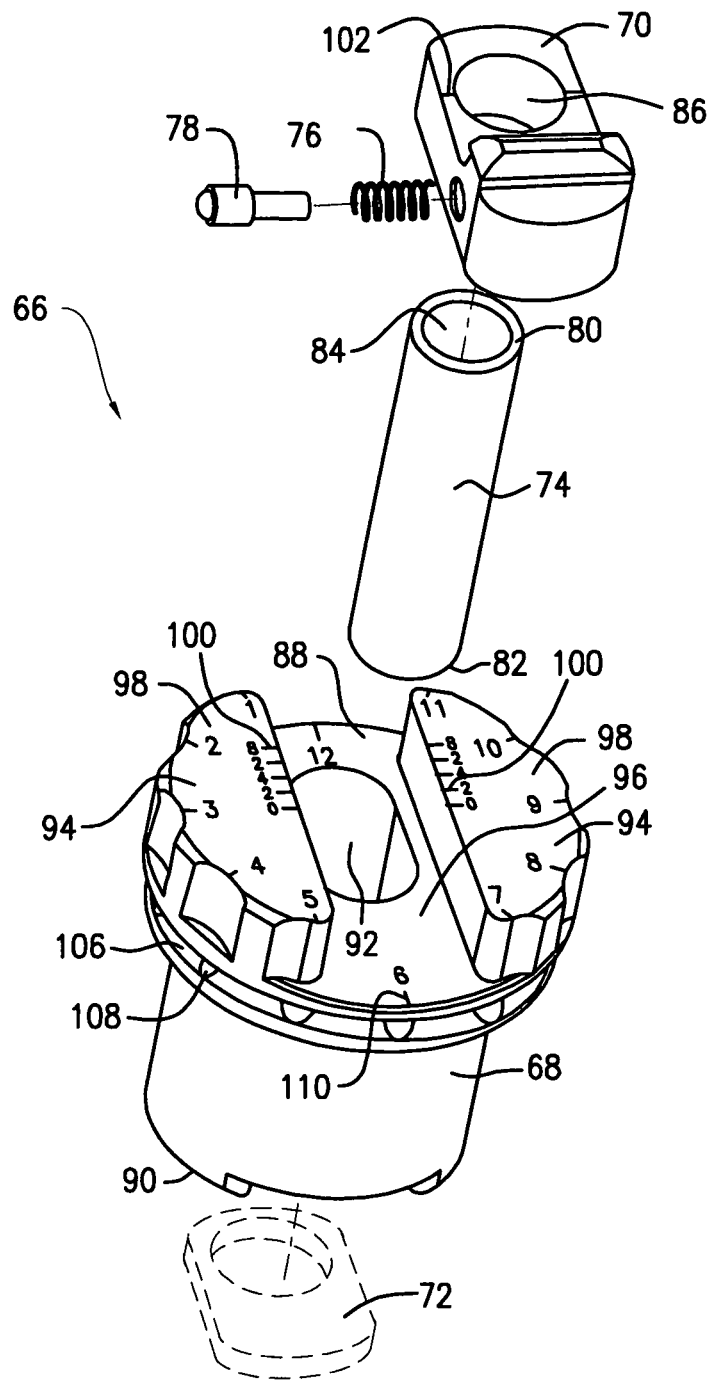
FIG. 3 is an exploded isometric view of the offset bushing assembly that can be rotatably inserted in bushing guide of FIG. 2.

FIG. 3 shows an exploded view of an assembly of an offset bushing 66. Offset bushing 66 includes a bushing body 68, a trigger flange 70, a bottom flange 72, a hollow cylindrical piece 74, a spring 76 and a spring loaded pin 78. Spring 76 and pin 78 are mounted inside trigger flange 70 such that the top of pin 78 projects out from side of trigger flange 70. Pin 78 can be pushed in by applying a force on its exposed tip, however, spring 76 would push it in a direction away from trigger flange 70 at all times. Hollow cylindrical piece 74 has top end 80 and bottom end 82. Top end 80 is attached to trigger flange 70 in any suitable manner including welding and press fitting. When attached to trigger flange 70, bore 84 of cylindrical piece 74 is aligned with bore 86 formed in trigger flange 70.

Bushing body 68 includes a first end 88 and a second end 90. A slot 92 is formed in body 68. Slot 92 extends from first end 88 to second end 90. Two raised portions 94 are formed on opposing side of slot 92. Vertical sides of raised portions 94 face each other and form a slot 96 between them. Top surfaces 98 of raised portions 94 have indicia 100.

The assembly of trigger flange 70, cylindrical piece 74, spring 76 and pin 78 is inserted in slot 92 such that bottom end 82 of cylindrical piece 74 is close to second end 90 of bushing body 68. Bottom flange 72 is attached to bottom end 82 in any suitable manner, including welding, to capture bushing body 68 between trigger flange 70 and bottom flange 72. In this assembled state, trigger flange 70 can slide back and forth in slot 96. An indicia 102 is formed on the upper surface of trigger flange 70. Indicia 102 is aligned with the center of bore 86. Indicia 102 when aligned with one of indicia 100 measures the offset of center of bore 86 from center of bushing body 68. The offset can vary between zero and eight millimeters or may be more than eight millimeters. Trigger flange 70 may slide freely in slot 96 or may slide in a stepwise manner. When trigger flange 70 is configured to slide stepwise, detents 104 (see FIG. 3A) are formed on vertical side of a raised portion 94. Trigger flange 70, when pushed, will slide the distance between adjacent detents 104. Trigger flange 70 would be locked in place due to pin 78 being engaged in detent 104. Only upon applying force sufficient to overcome the spring force, trigger flange 70 would slide so that pin 78 would engage the next detent 104. In another embodiment, pin 78 may not be spring loaded. Pin 78 may be pushed in to lock trigger flange in place.

Bushing body 68 has a groove 106 around its periphery near first end 88. Multiple detents 108 are formed in groove 106. Bushing body 68 forms a sliding fit in opening 48 in bushing guide 42. When bushing body 68 is placed in opening 48, groove 106 and detents 108 are aligned with pin 58. Thus, bushing body 68 can rotate around its longitudinal axis in opening 48 with pin 58 riding in groove 106. In a free floating version, detents 108 are not formed and therefore, bushing 68 can freely rotate in opening 48. When detents 108 are present, bushing body 68 rotates in opening 48 in a stepwise manner, with each step being the distance between adjacent detents 108. Indicia 110 may be associated with one or more detents 108. Alignment of indicia 110 with a fixed point such as pin 58 may be used to indicate the orientation of the center of hole 86 with respect to the center of bushing body 68.

Figure 3A:
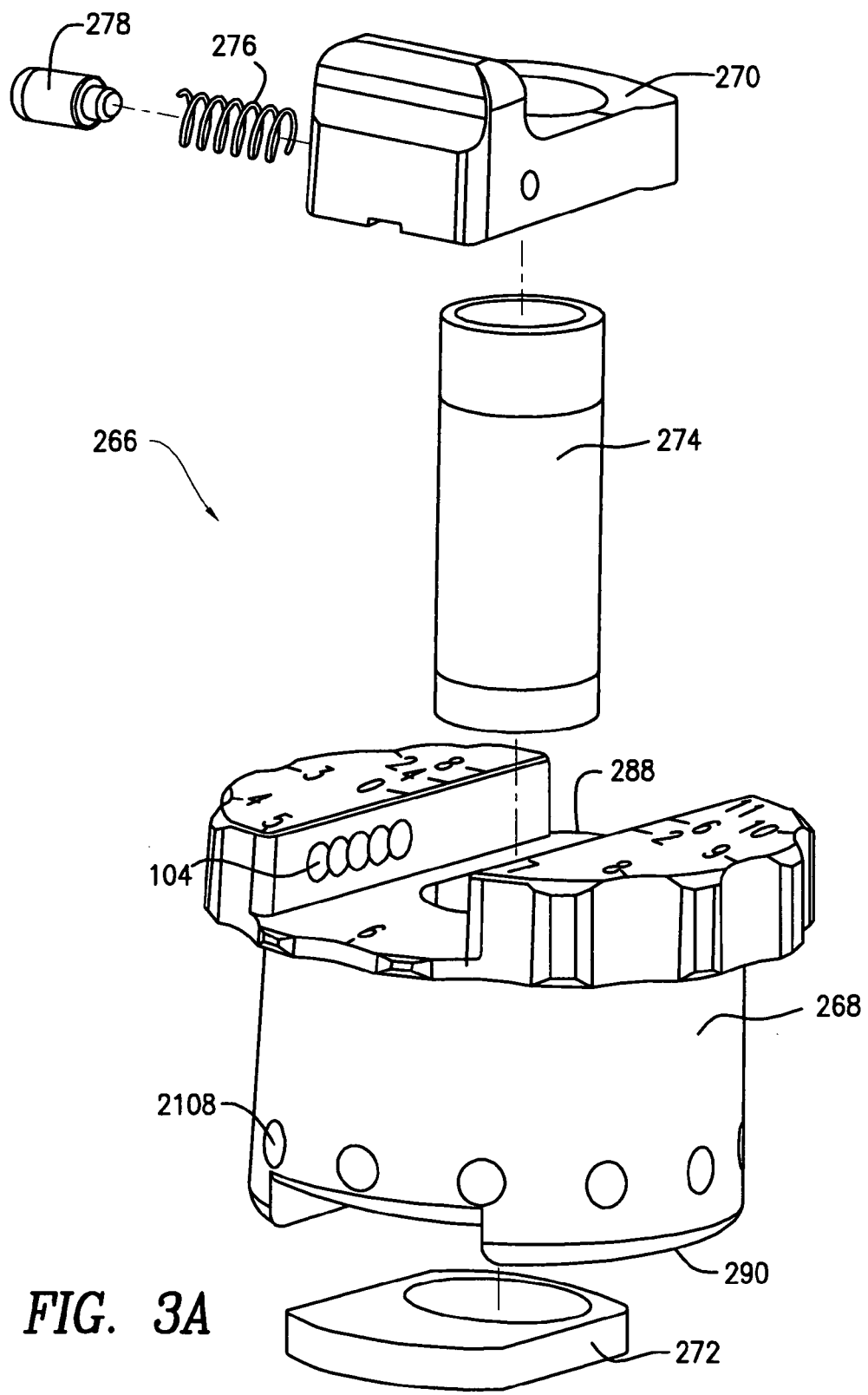
FIG. 3A is an exploded isometric view of another embodiment of the offset bushing assembly that can be rotatably inserted in bushing guide of FIG. 2.

FIG. 3A shows an exploded view of another embodiment of the assembly of offset bushing 66. This embodiment includes offset bushing 266 having a bushing body 268, a trigger flange 270, a bottom flange 272, a hollow cylindrical piece 274, a spring 276 and a spring loaded pin 278. The assembly of offset bushing 66 and the assembly of offset bushing 266 are similar except for the features discussed hereafter. Bushing body 268 has a first end 288 and a second end 290. Multiple detents 2108 are formed on bushing body 268 close to second end 290. Detents 2108 would be across from pin 258 when offset bushing 266 is assembled with bushing guide 242. The method of use of offset bushing 266 and offset bushing 66 are substantially similar.

Figure 4:
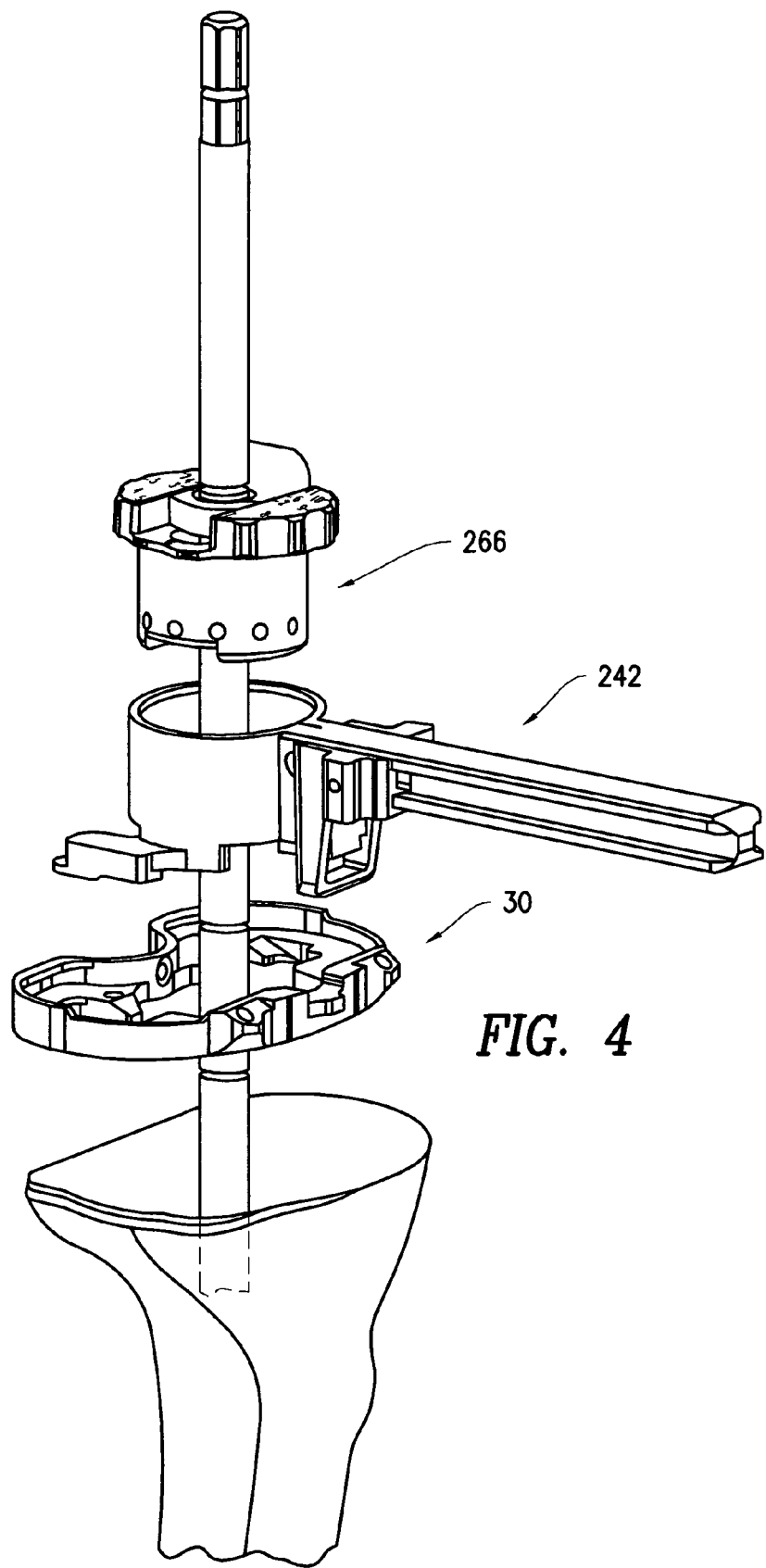
FIG. 4 is an exploded view illustrating mounting of the tibial plate, bushing guide and the offset bushing on a bone.

In use, (see FIG. 4) tibial template 30, bushing guide 42 and offset bushing 66 are assembled together. Next, the assembly is passed over a reamer shank onto the bone. (Any suitable intramedullary reference such as an intramedullary rod, stem trial or stem extender shaft may be used in place of the reamer) This is achieved by sliding the reamer shank in bore 84 of cylindrical piece 74. The reamer, at this time, is located in the intramedullary canal. Tibial template 30 is positioned for best coverage of the resected bone surface. This is achieved by rotating bushing body 68 and translating trigger flange 70 to find the setting for which optimum bone coverage is obtained. Tibial template 30 is pinned in this position and setting for offset is recorded by noting indicia 100 that corresponds to indicia 102. The orientation is recorded by noting indicia 110 that corresponds to a fixed point such as pin 58. The offset and orientation together represent the location of the center of the intramedullary canal as represented by the center of the stem of the reamer with respect to the center of offset bushing 66 which in turn may represent the center of the stem of a prosthetic device. Knowing the offset and orientation allows the surgeon to pick the correct part for the prosthetic to be implanted and assemble it in the right orientation.

In an alternative method of use, tibial template 30 is first placed over the bone and moved around to determine best coverage of resected surface of the bone. Tibial template 30 is pinned in this position and then bushing guide 42 is assembled with tibial template 30. Next, offset bushing 66 is assembled into bushing guide 42 by dropping it over the reamer shank so that reamer shank slides into bore 84. The reamer, at this time is located in the intramedullary canal. To assemble bushing 66, it may be necessary to rotate it and translate trigger flange 70. Once the assembly is complete the offset and orientation is noted as discussed previously.

The rotation of bushing 66 and sliding of trigger flange 70 may be stepwise or it may be "free-floating." In free-floating embodiment it may not be necessary to provide spring loaded pins 58 and 78. An alternative locking mechanism may be provided to lock bushing 66 and trigger flange 70 once the offset orientation has been set. The free-floating or the stepwise embodiment may be used in any of the methods described herein.

Figure 5:
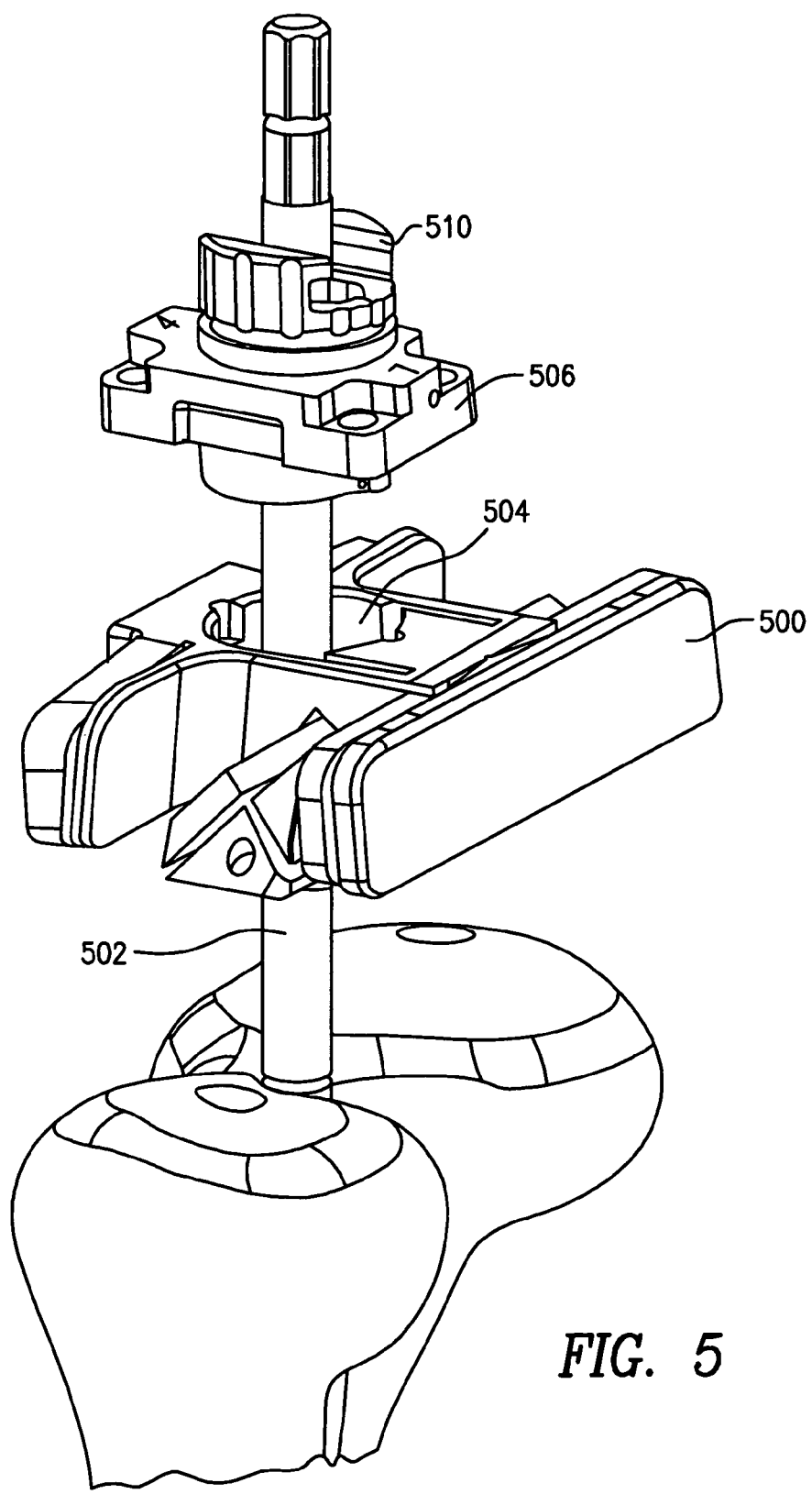
FIG. 5 is an exploded view illustrating mounting of the cutting guide, bushing guide and the offset bushing on a bone.
Figure 6:
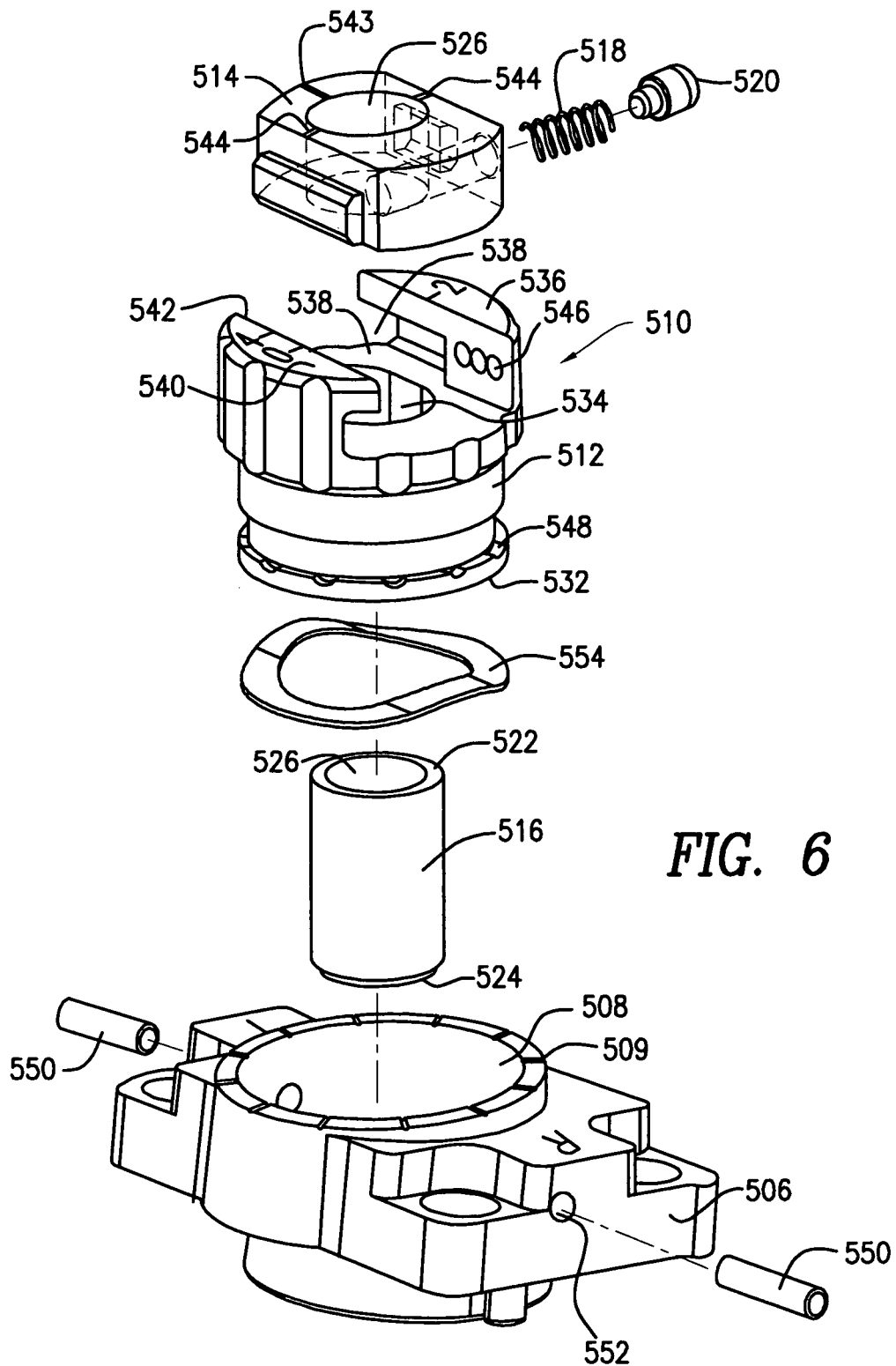
FIG. 6 is an exploded view showing bushing guide and various parts used in offset bushing assembly for use with cutting guide.

FIG. 5 shows a cutting guide 500. Cutting guide 500 is inserted over an intramedullary rod 502 that is inserted in a bone such as a femur. Cutting guide 500 is used to guide a blade for resection of the bone. Cutting guide 500 has a hole 504. A bushing guide 506 may be mounted in hole 504. A hole 508 (FIG. 6) is formed substantially in the center of bushing guide 506. A cylindrical wall surrounds hole 508. Indicia 509 are located on the wall surrounding hole 508. Each indicia 509 may be equidistant from its neighboring indicia 509. An offset bushing 510 is inserted in hole 508. Offset bushing 510 includes a bushing body 512, a trigger flange 514, a hollow cylindrical piece 516, a spring 518 and a spring loaded pin 520. Spring 518 and pin 520 are mounted inside trigger flange 514 such that the top of pin 520 projects out from side of trigger flange 514. Pin 520 works similar to pin 78 described previously. Hollow cylindrical piece 516 has top end 522 and bottom end 524. Top end 522 is attached to trigger flange 514 in any suitable manner including welding and press fitting. When attached to trigger flange 514, bore 526 of cylindrical piece 516 is aligned with bore 528 formed in trigger flange 514.

Bushing body 512 includes a first end 530 and a second end 532. A slot 534 is formed in body 512. Slot 534 extends from first end 530 to second end 532. Two raised portions 536 are formed on opposing side of slot 534. Vertical sides of raised portions 536 face each other and form a slot 538 between them. Top surfaces 540 of raised portions 536 have indicia 542.

The assembly of trigger flange 514, cylindrical piece 516, spring 518 and pin 520 is inserted in slot 538 such that bottom end 524 of cylindrical piece 516 is close to second end 532 of bushing body 512. In this assembled state, trigger flange 514 can slide back and forth in slot 538. An indicia 544 is formed on the upper surface of trigger flange 514. Indicia 544 is aligned with the center of bore 528. Indicia 544 when aligned with one of indicia 542 measures the offset of center of bore 528 from center of bushing body 512. The offset, for example, may vary between zero and eight millimeters. Trigger flange 514 may slide freely in slot 538 or may slide in a stepwise manner. When trigger flange 514 is configured to slide stepwise, detents 546 are formed on vertical side of a raised portion 536. Trigger flange 514, when pushed, will slide the distance between adjacent detents 546. Trigger flange 514 would be locked in place due to pin 520 being engaged in detent 546. Only upon applying force sufficient to overcome the spring force, trigger flange 514 would slide so that pin 520 would engage the next detent 546. Trigger flange 514 also has an indicia 543 located at the tip of trigger flange 514. Indicia 543 can align with indicia 509 to provide a measure of orientation of the center of bore 528 with respect to the center of hole 508.

Bushing body 512 has multiple detents 548 formed near its second end 532. Bushing body 512 slides in opening 508 in bushing guide 506. When bushing body 512 is placed in opening 508, detents 548 are aligned with pins 550 inserted in holes 552 formed in bushing guide 506. Bushing body 512 can rotate around its longitudinal axis in opening 508. Pins 550 may be pushed in to engage detents 548 and lock the bushing body in place. In a free floating version, detents 548 are not formed and therefore, bushing 512 can freely rotate in opening 508. A washer 554 may be placed between bushing guide 506 and bushing 510.

In use, an intramedullary reference such as an intramedullary reamer, intramedullary rod, stem trial or stem extender shaft is inserted in a bone such as a femur. Next, cutting guide 500 is inserted over the intramedullary reference so that the intramedullary reference passes through hole 504 in cutting guide 500. Cutting guide 500 is moved around to place it in the desired position that will result in correct resection of the bone. Cutting guide 500 is fixed to the bone in this position. Next, offset bushing 510 is inserted on the intramedullary reference such that the intramedullary reference passes through bore 526 in cylindrical piece 516. Alternatively, offset bushing 510 may be first inserted in bushing guide 506 and this assembly assembled with the cutting guide 500. Cutting guide 500, is inserted over the intramedullary reference so that the intramedullary reference passes through hole 504 in cutting guide 500 which in turn may be pinned to the bone. Trigger flange 514 is moved in slot 538 and bushing body 512 is rotated to allow insertion of offset bushing 510 in hole 508. The offset is noted by reading indicia 542 that corresponds to indicia 544. The orientation is noted by noting alignment between indicia 543 and one of the indicia 509. The offset and orientation together represent the location of the center of the intramedullary canal as represented by the center of the intramedullary reference with respect to the center of offset bushing 510 which in turn may represent the center of the stem of a prosthetic device. Knowing the offset and orientation allows the surgeon to pick the correct part for the prosthetic to be implanted and assemble it in the right orientation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A joint prosthesis instrument comprising:
    an intramedullary reference;
    a plate adapted to attach to a bone;
    a rotatable bushing having a top surface, a bottom surface, and an oblong hole extending between the top surface and the bottom surface, wherein the oblong hole has an elongated opening with elongated sides extending along the top surface, and wherein the rotatable bushing is adapted to rotate with respect to the plate; and
    a trigger flange slidably mounted in the bushing, the trigger flange having a first hole positioned along a length of the elongated opening of the oblong hole, the first hole being sized to allow the intramedullary reference to slide in the hole, wherein by rotating the bushing and sliding the trigger flange the first hole in the trigger flange can be located in a position that can receive the intramedullary reference, thereby measuring the angular orientation and linear distance of the intramedullary reference with respect to a fixed point on the plate.

2. The joint prosthesis instrument of claim 1, further comprising:
    a bushing guide, the bushing guide having a first opening to rotatably engage the rotatable bushing in the first opening.

3. The joint prosthesis instrument of claim 2, further comprising:
a second opening formed in the plate, at least a portion of the second opening being aligned with the first opening in the bushing guide.

4. The joint prosthesis instrument of claim 3, wherein at least a portion of the oblong hole is aligned with the first opening in the plate.

5. The joint prosthesis instrument of claim 4, further comprising:
first indentations formed on the bushing, the first indentations being spaced a fixed distance apart from each other.

6. The joint prosthesis instrument of claim 5, further comprising:
a handle attached to the bushing guide; and
a first spring loaded pin attached to the handle, wherein the first spring loaded pin engages the indentations on the bushing to lock the bushing in place.

7. The joint prosthesis instrument of claim 2, further comprising:
a top surface having markings used to determine linear distance by which the intramedullary reference is offset from the fixed point on the plate.

8. The joint prosthesis instrument of claim 7, further comprising:
at least one raised portion formed on the bushing, the raised portion having a side surface, a second indentations formed on the side surface of the raised position;
a second spring loaded pin mounted on the trigger flange, the second spring loaded pin engaging the second indentations to lock the trigger flange in place.

9. A joint prosthesis instrument comprising:
an intramedullary reference;
an intermediary piece adapted to attach to a bone;
a rotatable bushing adapted to rotate with respect to the intermediary piece, the rotatable bushing having an outer surface; and
a trigger flange slidably mounted in the bushing, the trigger flange having a first hole, the first hole being sized to allow the intramedullary reference to slide in the hole, wherein by rotating the bushing and sliding the trigger flange in a longitudinal direction across at least a portion of the outer surface of the rotatable bushing, the intramedullary reference can be being positioned within the first hole in the trigger flange, thereby measuring the angular orientation and linear distance of the intramedullary reference with respect to a fixed point on the intermediate piece.

10. The joint prosthesis instrument of claim 9, wherein the intermediary piece is selected from a group consisting of a tibial plate and a cutting guide.

11. The joint prosthesis instrument of claim 10, further comprising:
a bushing guide, the bushing guide having a first opening to rotatably engage the rotatable bushing in the first opening.

12. The joint prosthesis instrument of claim 11, further comprising:
a second opening formed in the intermediate piece, at least a portion of the second opening being aligned with the first opening in the bushing guide.

13. The joint prosthesis instrument of claim 12, wherein the rotatable bushing has an oblong hole, and at least a portion of the oblong hole is aligned with the first opening in the intermediate piece.

14. The joint prosthesis instrument of claim 13, further comprising:
first indentations formed on the rotatable bushing, the first indentations being spaced a fixed distance apart from each other.

15. The joint prosthesis instrument of claim 14, further comprising:
a pin insertable in the bushing guide, wherein the pin engages the indentations on the bushing to lock the bushing in place.

16. The joint prosthesis instrument of claim 11, further comprising:
markings used to determine linear distance by which the intramedullary reference is offset from the fixed point on the intermediate piece.

17. The joint prosthesis instrument of claim 16, further comprising:
second indentations formed on the side surface of the rotatable bushing that faces the side surface of the trigger flange;
a spring loaded pin mounted on the trigger flange, the spring loaded pin engaging the second indentations to lock the trigger flange in place.

18. The joint prosthesis instrument of claim 9, wherein the rotatable bushing further comprises a bushing body having a recess, wherein the trigger flange is positioned within said recess of the bushing body and is capable of sliding within the recess.

19. The joint prosthesis instrument of claim 1, further comprising an axis extending through the oblong hole and wherein the first hole is aligned with the axis.

20. The joint prosthesis instrument of claim 1, wherein when the bushing is rotated and the trigger is slid, the first hole in the trigger flange is aligned with the intramedullary reference.

21. The joint prosthesis instrument of claim 9, wherein the trigger flange has a top surface and a bottoms surface, and wherein when the trigger flange is slid in the longitudinal direction across at least a portion of the outer surface of the rotatable bushing, the bottom surface of the trigger flange moves across at least a portion of the outer surface.

22. The joint prosthesis instrument of claim 9, wherein the rotatable bushing further includes an interior hole and wherein when the trigger flange is slid in a longitudinal direction across at least a portion of the outer surface of the rotatable bushing, the first hole in the trigger flange can be axially aligned with at least a portion of the interior hole.

* * * * *